(12) United States Patent
Nevo

(10) Patent No.: US 9,566,047 B2
(45) Date of Patent: Feb. 14, 2017

(54) CRYOGENIC BIOPSY SYSTEM AND METHOD

(76) Inventor: Erez Nevo, Baltimore, MD (US)

(*) Notice: Subject to any disclaimer, the term of this patent is extended or adjusted under 35 U.S.C. 154(b) by 1033 days.

(21) Appl. No.: 13/581,311

(22) PCT Filed: Feb. 25, 2011

(86) PCT No.: PCT/IB2011/050805
§ 371 (c)(1),
(2), (4) Date: Aug. 26, 2012

(87) PCT Pub. No.: WO2011/104692
PCT Pub. Date: Sep. 1, 2011

(65) Prior Publication Data
US 2012/0322070 A1    Dec. 20, 2012

Related U.S. Application Data

(60) Provisional application No. 61/307,884, filed on Feb. 25, 2010.

(51) Int. Cl.
| | |
|---|---|
| *A61B 10/00* | (2006.01) |
| *A61B 10/02* | (2006.01) |
| *A61B 17/32* | (2006.01) |
| *A61B 18/02* | (2006.01) |

(52) U.S. Cl.
CPC ....... *A61B 10/0275* (2013.01); *A61B 10/0266* (2013.01); *A61B 17/32002* (2013.01); *A61B 18/02* (2013.01)

(58) Field of Classification Search
CPC ............ A61B 10/0266; A61B 10/0041; A61B 10/0275; A61B 17/32053; A61B 2010/0208; A61B 2018/0293; A61B 2018/0262; A61B 2017/00199
USPC .................. 600/564–568; 606/167, 170, 171
See application file for complete search history.

(56) References Cited

U.S. PATENT DOCUMENTS

| | | |
|---|---|---|
| 6,248,081 B1 | 6/2001 | Nishtalas et al. |
| 6,551,255 B2 | 4/2003 | Van Bladel et al. |
| 2003/0208135 A1 | 11/2003 | Bloom et al. |
| 2005/0101879 A1 | 5/2005 | Shidham et al. |
| 2005/0113854 A1* | 5/2005 | Uckele ............... A61B 10/0266 606/167 |
| 2007/0055173 A1 | 3/2007 | DeLonzor |
| 2007/0116612 A1 | 5/2007 | Williamson IV |

(Continued)

FOREIGN PATENT DOCUMENTS

WO    WO 03/026476    10/2003

*Primary Examiner* — Max Hindenburg
*Assistant Examiner* — Jonathan M Foreman
(74) *Attorney, Agent, or Firm* — Daniel J. Swirsky; AlphaPatent Associates Ltd.

(57) ABSTRACT

A cryogenic biopsy device is configured to provide thin, frozen tissue samples, which may be viewed under a microscope and selected for biomarker analysis. The device is configured to provide slices which are less than 50 micrometers in thickness, while snap-freezing the tissue and maintaining the sample in a deep-frozen state until it reaches the pathology lab for further processing. Alternatively, thicker slices can be harvested by the device and additional sectioning can be done in the pathology lab by using cryomicrotome. The device of the present invention may be used in rigid instruments and in flexible devices, such as endoscopes, for example, and may be suitable for single use or multiple use.

20 Claims, 13 Drawing Sheets

(56) References Cited

U.S. PATENT DOCUMENTS

| | | |
|---|---|---|
| 2007/0156125 A1 | 7/2007 | DeLonzor |
| 2007/0158147 A1 | 7/2007 | Heske et al. |
| 2007/0191732 A1 | 8/2007 | Voegele |
| 2008/0026420 A1* | 1/2008 | Rimm ................. G01N 21/6458 435/40.5 |
| 2008/0188767 A1* | 8/2008 | Oaki ...................... A61B 1/018 600/566 |
| 2008/0281225 A1 | 11/2008 | Spero et al. |
| 2008/0306405 A1 | 12/2008 | Masseglia et al. |
| 2009/0054806 A1 | 2/2009 | Gellman et al. |
| 2010/0041094 A1* | 2/2010 | Sukumar .................. B60P 3/14 435/40.52 |

\* cited by examiner

CRYOGENIC BIOPSY SYSTEM AND METHOD

The present application is a U.S. National Phase Application under 35 U.S.C. 371 of PCT International Application No. PCT/IB2011/050805, which has an international filing date of Feb. 25, 2011, and which claims priority from U.S. Provisional Patent Application No. 61/307,884, filed Feb. 25, 2010, the contents of which are incorporated herein by reference.

FIELD OF THE INVENTION

The present invention relates to a cryogenic biopsy system and method, and, more particularly to a system and method for preserving bio-markers in a biopsy tissue and optimization of analysis of the bio-markers via freezing and thin slicing.

BACKGROUND OF THE INVENTION

Molecular medicine holds much promise for advancing cancer diagnosis and treatment if biomarkers, molecular targets and drug effects on these targets can be accurately assessed in tumors. The amount and function of molecular drug targets within signal transduction pathways are often regulated by rapid enzymatic reactions in response to physiological stimuli. Biopsies play a central role in assessing biomarkers and molecular targets in solid tumors, but the traumatic process of cutting tissue samples by current biopsy devices perturb the tumor environment and thereby induce extraneous and confounding molecular responses to tissue trauma, bleeding and ischemia. Expeditious processing of the biopsy specimen using snap freezing or rapid fixation following tissue harvesting may be ineffective for preventing many rapid enzymatic modifications, because time frames of biopsy procedures and tissue handling before they are processed in the lab are longer than that of the enzymatic reactions. Moreover, artifacts from healthy tissue may reduce the accuracy of some types of biomarker analyses.

A method for tumor biopsy that preserves the molecular profile may facilitate pharmacodynamic assessment of targeted therapeutics and may also enable individualized molecular therapy of solid tumors based on accurate information about signal transduction pathways, molecular drug targets and biomarkers. This can maximize the efficacy of new directed chemotherapy agents by choosing the most appropriate patients for each type of therapy. As most of these therapies are associated with severe adverse effects and are highly expensive, individually directed therapy may eliminate suffering in patients that will not benefit from these therapies and can substantially reduce healthcare costs.

Many cancer patients do not benefit from the systemic treatments they receive. For example, an adjuvant chemotherapy regimen that is considered highly effective may often improve the disease-free or overall survival rate by only few percent. Also, chemotherapy for metastatic disease often provides sustained benefit for a small portion of the patients treated. Therefore, the medical therapies currently available to clinical practice expose far more patients than will benefit to the cost and toxicity of these agents. Although this over treatment is understandable in dealing with life-threatening diseases, the ability to better personalize treatment decisions could have important benefits for patients as well as reduce medical costs.

Biomarkers can be classified into two classes based on their mode of analysis: 1. Histology-based biomarkers adhere to specific structures in the tissue (e.g. cell membranes, chromosomes) and thus require intact tissue (e.g. immunohistochemical (IHC) and fluorescent in-situ hybridization (FISH)). In these tests tissue fixation can be done by chemicals (e.g. formalin-fixed paraffin-embedded, FFPE) or by freezing (e.g. frozen sections). These techniques can identify single or groups of cancerous cells in otherwise healthy tissue and may enable early detection of cancer. However, its processing is currently manual, time consuming and is difficult to standardize and quantify. 2. Content-based biomarkers are determined as the tissue concentration of specific molecules (e.g. proteins, RNA and DNA) that either have altered structure (e.g. DNA alterations) or abnormal levels in tumor cells. These biomarkers do not require the use of intact tissue, and typically involve tissue homogenate that is achieved by sample pulverization in the lab. Most of the studies on proteomic and genomic profiling of malignant tumors have been based on whole-tissue homogenate. However, their sensitivity may be reduced when non-homogenous tissue samples with a mixture of normal and cancerous cells are analyzed. It would be advantageous to have a biopsy system which enables preservation of biomarkers.

A cryogenic biopsy device is disclosed in U.S. Pat. No. 6,551,255. The device is configured for securing and coring of tumors within the body. An adhesion probe provides a coolant for adhering to the tumor and easing attachment of the tumor to the probe. However, the device disclosed therein does not disclose a system and method for providing frozen samples of tissue which may be analyzed histologically as well as via biomarker analysis while maintaining the molecular profile of the sample.

Thus, there is a need for a system and method for obtaining samples for content-based biomarker analysis wherein the molecular profiles of the samples can be stabilized during the procedure, and wherein sensitivity of bio-marker analysis is enhanced by providing more homogenous tissue samples.

SUMMARY OF THE INVENTION

There is provided, in accordance with embodiments of the present invention, a cryogenic biopsy device. The device includes a cutting portion positioned at a distal end of the device and a gear mechanism. The cutting portion includes a cryogenic needle having a needle tip configured to penetrate a tissue to be sampled and configured to freeze the tissue to a temperature of less than −10 degrees Celsius, a slicer coaxial to the cryogenic needle, slicer configured to slice a sample of the tissue via a rotating mechanism, and a collection compartment coaxial to the cryogenic needle for collecting the sample tissue. The gear mechanism is configured for advancing the slicer rotationally and translationally.

In accordance with further features in embodiments of the present invention, the cryogenic needle may have a diameter of 1.5 mm or less, or of any other suitable diameter. The cryogenic needle further includes a hollow portion for introduction of a freezing gas therein. The tissue sample may have a thickness of 50 micrometers or less and in some embodiments may have a thickness of approximately 10 micrometers. According to further features, the device may further include a sensor at the needle tip. The sensor in some embodiments may be a temperature sensor.

In accordance with further features in embodiments of the present invention, the gear mechanism may have a pinion and wheel configuration. The gear mechanism may also include a threaded bar attached to the wheel, and positioned through a nut on the device body. The threaded bar may rotatably pass through the nut upon activation of the gear mechanism. The gear mechanism is configured to provide rotational and translational movement of the slicer simultaneously.

In accordance with further features in embodiments of the present invention, the collection compartment may be a sheath positioned coaxial to the slicer. In accordance with other embodiments, the collection compartment may be a collection vial. In some embodiments, the slicer has a helical flute configuration. In other embodiments, the slicer has a cutting head and blades. The cutting head may be a stationary cutting head and the blades may be configured to rotate. Alternatively, the cutting head may be a rotating cutting head. The body of the device as well as the cryogenic needle may be flexible for use in an endoscope, for example.

There is provided, in accordance with another embodiment of the present invention, a biopsy system. The system includes a freezing unit, a cryogenic needle in fluid communication with the freezing unit, a slicer positioned coaxial to the cryogenic needle for providing frozen sliced samples of tissue, a collection compartment for collecting the sliced samples of tissue, wherein the collection compartment is configured to maintain a frozen state of the sliced samples, a microscopy device for viewing the samples, and a biomarker analysis mechanism for analysis of at least some of the frozen and viewed samples.

In accordance with further features in embodiments of the present invention, the freezing unit may include a freezing substance compartment and a processor. In some embodiments, the system further includes a sensor positioned on the cryogenic needle, wherein the sensor is in electronic communication with the processor and is configured to provide feedback to the processor. The processor may be configured to regulate a freezing temperature based on the feedback. In some embodiments, the system further includes a dispenser to prevent curling of frozen tissue samples. In some embodiments, the system further includes a selector for selecting samples for biomarker analysis based on the viewed samples.

There is provided, in accordance with yet another embodiment of the present invention, a method of analyzing a tissue sample. The method includes providing a frozen tissue sample, wherein histological parameters are maintained, viewing the frozen tissue sample under microscopy, selecting a portion of the viewed frozen sample for analysis, and analyzing the selected portion for biomarkers.

In accordance with further features in embodiments of the present invention, the steps of providing, viewing, selecting and analyzing are all done while the tissue sample is maintained at a frozen temperature. In some embodiments, the tissue sample is maintained at a temperature of −10 degrees Celsius or less. In some embodiments, the providing of a frozen tissue sample is done with a cryogenic biopsy device. In some embodiments, the frozen tissue sample may have a thickness of less than 50 micrometers. In other embodiments, the slicing of the sample into sections having a thickness of less than 50 micrometers can be done prior to viewing. The selecting can be done by a user or via an automated system.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the present invention may be better understood by referring to the following description in conjunction with the accompanying drawings in which.

Figure 1:
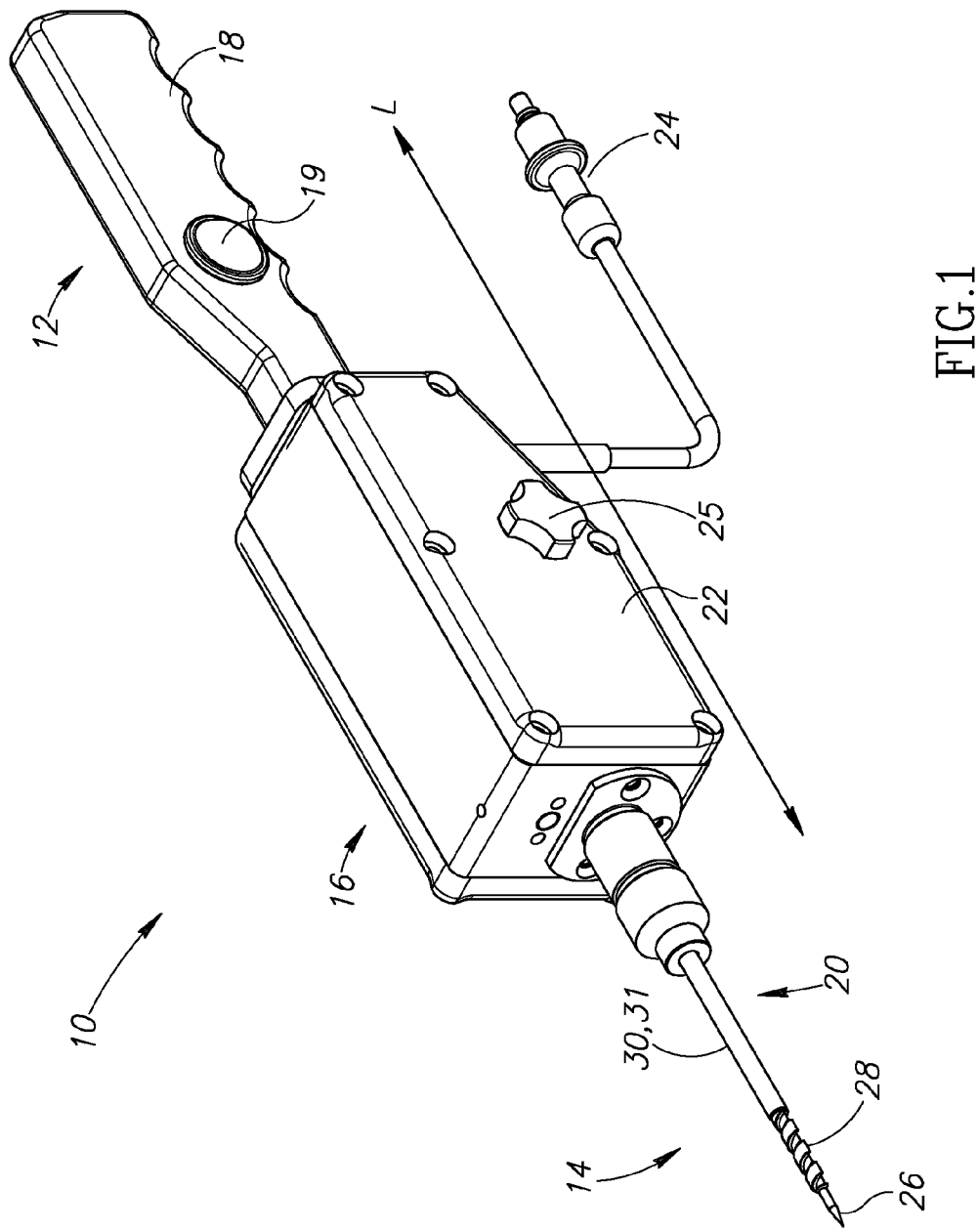
FIG. 1 is a schematic illustration of a biopsy device in accordance with embodiments of the present invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF THE INVENTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

Embodiments of the present invention are directed to systems and methods for biopsy and analysis of a tissue sample, and more particularly to a cryogenic biopsy device and method of analysis. The device and method of the present invention are designed to provide samples which can be used for both microscopic and biomarker analysis. The principles and operation of systems and methods according to the present invention may be better understood with reference to the drawings and accompanying descriptions.

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

A device in accordance with embodiments of the present invention is a cryogenic biopsy device that can snap-freeze the tissue and maintain the sample in a deep-frozen state until it reaches the pathology lab for further processing. The device of the present invention may be used in rigid instruments and in flexible devices, such as endoscopes, for example, and may be suitable for single use or multiple use.

The present invention aims to stabilize tissue biomarkers based on rapid, deep freezing of the tissue. To eliminate any change due to the traumatic cutting action itself, the deep-freeze of the tissue is done in-situ, before tissue harvesting, by using a cryogenic device. Tissue freezing within a few seconds stabilizes all cellular biochemical processes and ensures stabilization of protein-, RNA- and DNA-based biomarkers.

The use of a cryogenic biopsy device, such as the one described herein, provides better results than conventional biopsy procedures for assessing highly dynamic molecular profiles that are associated with a high degree of instability due to tissue injury.

Figure 2:
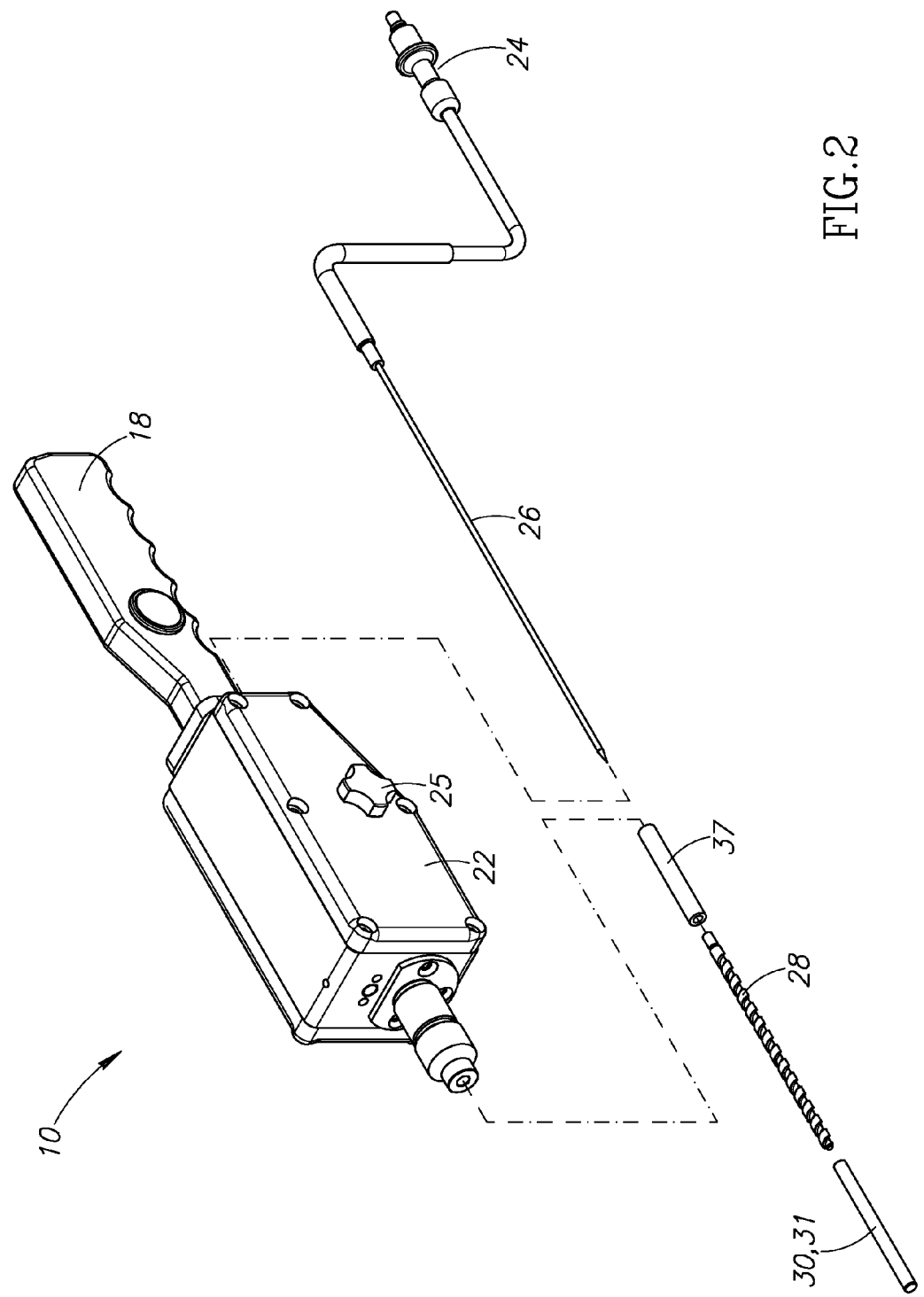
FIG. 2 is a schematic illustration of the device of FIG. 1, shown with portions removed to further illustrate these portions of the device.
Figure 6:
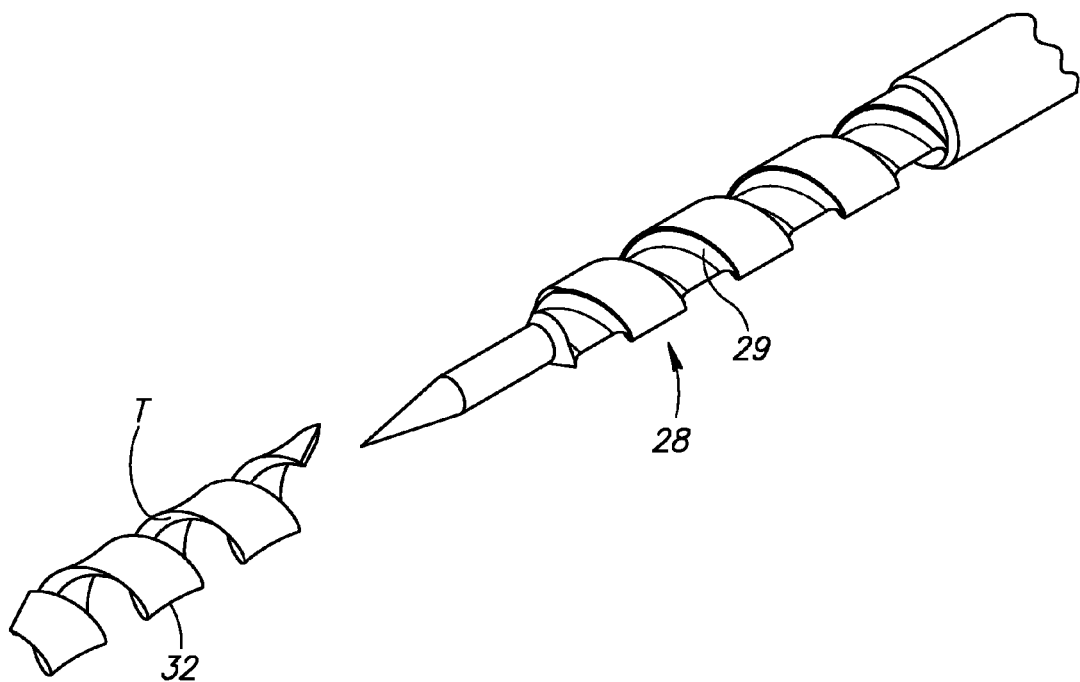
FIG. 6 is an expanded view of a slicer from the device of FIG. 1, and a sample resulting from a tissue sample sliced with the slicer.
Figure 7:
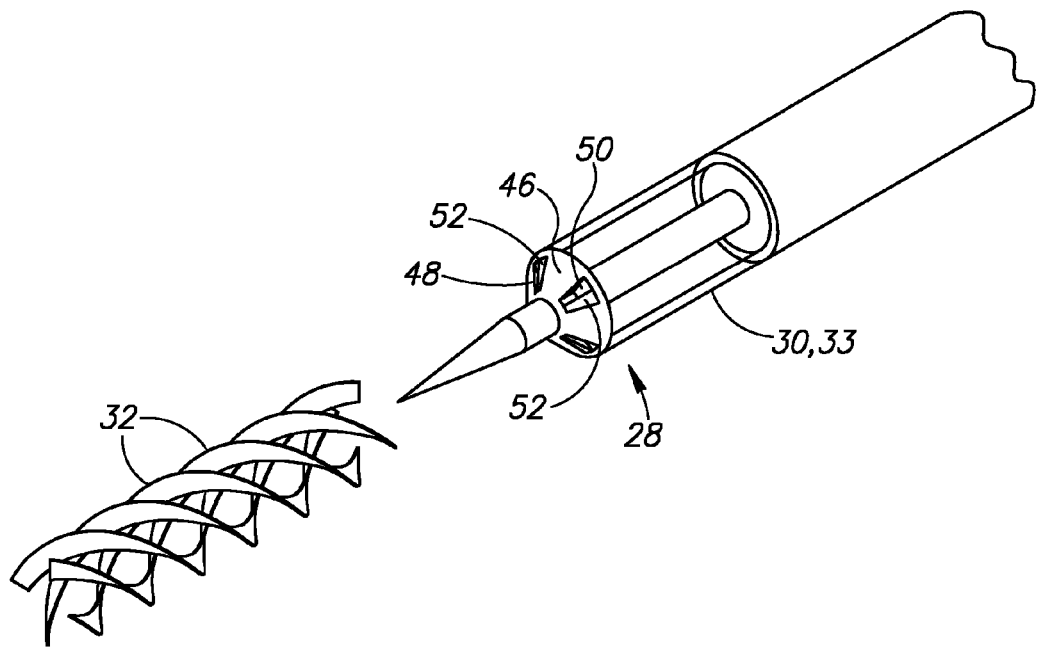
FIG. 7 is an expanded view of a slicer in a cutting-head configuration and a sample resulting from a tissue sample sliced with the slicer in accordance with additional embodiments of the present invention.

Reference is now made to FIG. 1, which is a schematic illustration of a biopsy device 10 in accordance with embodiments of the present invention. Device 10 has a proximal end 12, a distal end 14, and a middle portion 16 connecting proximal end 12 to distal end 14. Distal end 14 is defined as the portion of device 10 which enters the body and contacts the tissue to be biopsied. Proximal end 12 is defined as the portion of device 10 which is outside of the body and closest to the user. Proximal end 12 includes a handle 18 for holding of device 10 and further includes an activation switch 19. Distal end 14 includes a cutting portion 20, which will be described in greater detail hereinbelow. Middle portion 16 has a housing 22 which houses a mechanism for operation of cutting portion 20. A port 24 is positioned proximal to middle portion 16, and is used to connect a cryogenic needle 26 to a freezing unit, as will be described in greater detail with reference to FIG. 3. Cutting portion 20 includes a slicer 28 coaxially positioned with respect to cryogenic needle 26, and is designed to slice tissue into thin slices. Cutting portion 20 further includes a collection compartment 30 for holding tissue slices therein during the procedure and as device 10 is removed from the body. In one embodiment, as shown in FIG. 1, collection compartment 30 is a sheath 31 positioned around slicer 28. In another embodiment, collection compartment 30 may be a collection vial attached to slicer 28. Slicer 28 may include a rotatable cutting mechanism or a translational cutting mechanism or a combination thereof. In one embodiment, as shown in FIGS. 1, 2, and 6, slicer 28 has a rotatable helical flute configuration. In another embodiment, as shown in FIGS. 7 and 8, slicer 28 includes a cutting head which may be rotatable or may include rotational blades, as will be described in further detail hereinbelow. The resulting sample is held within collection compartment 30.

Reference is now made to FIG. 2, which is a schematic illustration of the device of FIG. 1, shown with port 24 and cryogenic needle 26 removed, and with slicer 28 and sheath 31 removed, to further illustrate these portions of device 10. Port 24 allows for introduction of a freezing substance to cryogenic needle 26. Cryogenic needle 26 may be, for example, a clinical grade 17-gauge cryotherapy needle (Galil Medical, Inc., Arden Hills, Minn.), having a diameter of approximately 1.5 mm. In some embodiments, cryogenic needle 26 is another commercially available needle or may be constructed specifically for the present invention. In some embodiments, a smaller diameter cryogenic needle may be used. For example, a cryogenic needle having an inner diameter of 0.3-0.4 mm would allow the overall size of device 10 to be in a range of 17-18 Gauge. In other embodiments, a larger diameter cryogenic needle 26 may be used. Cryogenic needle 26 may be any size needle suitable for a cryogenic biopsy procedure. Cryogenic needle 26 has a needle tip 60 at its distal end. Needle tip 60 is configured to penetrate the tissue to be sampled.

Cryogenic needle 26 may be secured in position by a fastener 25. Fastener 25 may be, for example, a knob or a snap ring. In the embodiments shown herein, fastener 25 is positioned on housing 22. However, it should be readily apparent that fastener 25 may be positioned in any suitable location on device 10. Fastener 25 may be used to secure cryogenic needle 26 during the procedure and may be released thereafter when the harvested tissue is removed from device 10.

Figure 3:
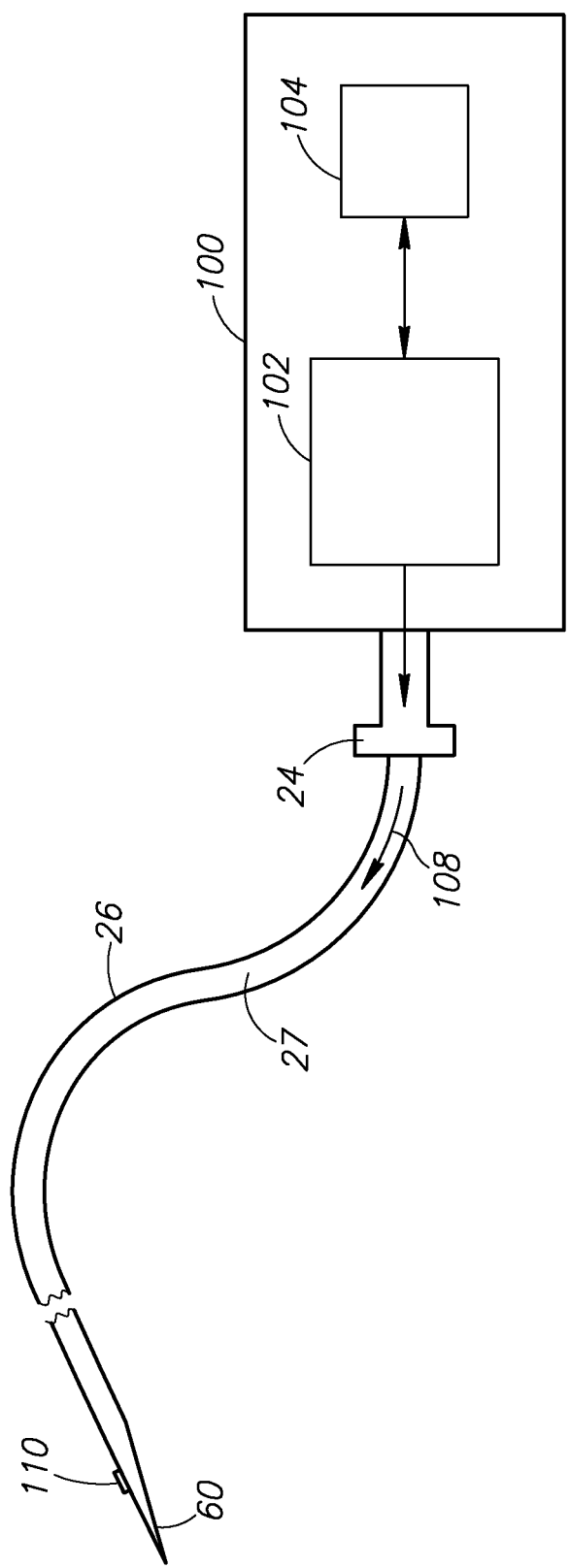
FIG. 3 is a block-diagram illustration of a freezing unit, in accordance with embodiments of the present invention.

Reference is now made to FIG. 3, which is a block-diagram illustration of a freezing unit 100, in accordance with embodiments of the present invention. Freezing unit 100 is an external unit which is connected to cryogenic needle 26 via port 24. In this embodiment, cryogenic needle 26 has a hollow portion 27 therethrough, through which a freezing substance may be inserted, as indicated by arrow 108. Freezing unit 100 may include a freezing substance compartment 102 and a processor 104. Freezing substance compartment 102 is configured to hold a freezing substance, such as Argon gas, for example. The freezing substance is introduced through port 24 into cryogenic needle 26. Optionally, processor 104 may regulate an amount and flow rate of freezing substance to enable control of the tissue freezing process (e.g. rate and magnitude of temperature drop). In some embodiments, a sensor 110 may be positioned at needle tip 60. Sensor 110 may be, for example, a multi-point thermal sensor (MTS). Sensor 110 may be in electronic communication with processor 104, and may be used to provide feedback regarding temperature of needle tip 60. Processor 104 can then make adjustments regarding the amount of freezing substance to release or the rate of release or other parameters.

Figure 4A:
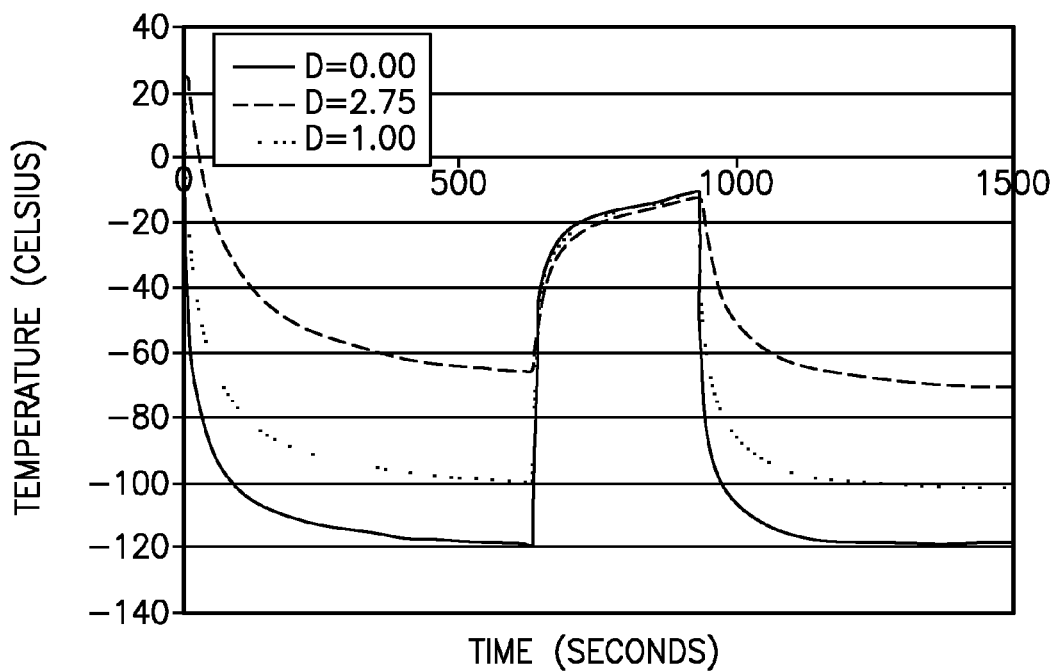
FIGS. 4A and 4B are graphical illustrations of temperature curves at distances from a needle surface.
Figure 4B:
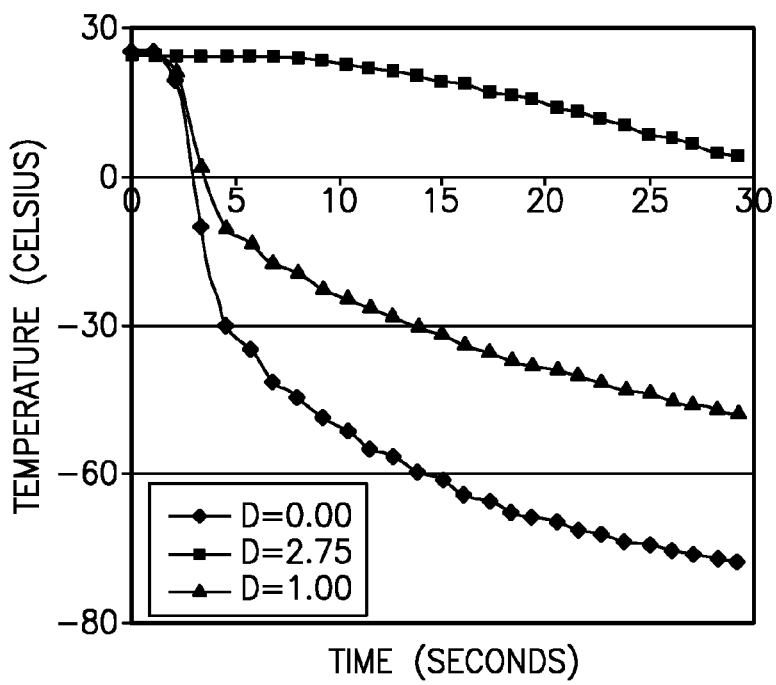

Tissue should be frozen to a temperature of −10 to −50 degrees Celsius in order to sufficiently preserve the biomolecular processes of the tissue. Tissue freezing to a temperature of −30° C. can be achieved at a distance of 1 mm from the surface of cryogenic needle 26 within approximately 15 seconds by commercially available cryo-ablation apparatus (e.g. SeedNet system, Galil Medical, Inc., Arden Hills, Minn.). Reference is now made to FIGS. 4A and 4B, which are graphical illustrations of temperature curves at distances from a needle surface. These measurements were made by Galil Medical using a cryo-ablation needle such as the one disclosed for use in the cryogenic biopsy device of the present invention. As shown in FIG. 4A, temperature curves at the needle surface and at a distance of 2.74 mm from the surface were measured. As shown in FIG. 4B, a temperature curve at a distance of 1 mm from the surface was interpolated from the two measured curves. At a temperature of −30° C., which is around the eutectic point of the intracellular and extracellular fluids, all intracellular biochemical processes cease and biomarker levels stabilize.

Freezing may be done by using compressed Argon gas through the Joule-Thomson effect to produce extremely low temperatures (−130° Celsius at the surface of cryogenic needle 26), or by other gases (e.g. Nitrogen, CO2). As the gas passes through cryogenic needle 26, needle tip 60 is cooled, forming an iceball, which stabilizes the intracellular biomolecular processes of the tissue. It should be readily apparent that any type of cryogenic method is included within the scope of the invention, including gases such as Nitrogen, Helium, Argon, CO2, electric cooling (e.g. Peltier cooler), or any other suitable method.

Figure 5A:
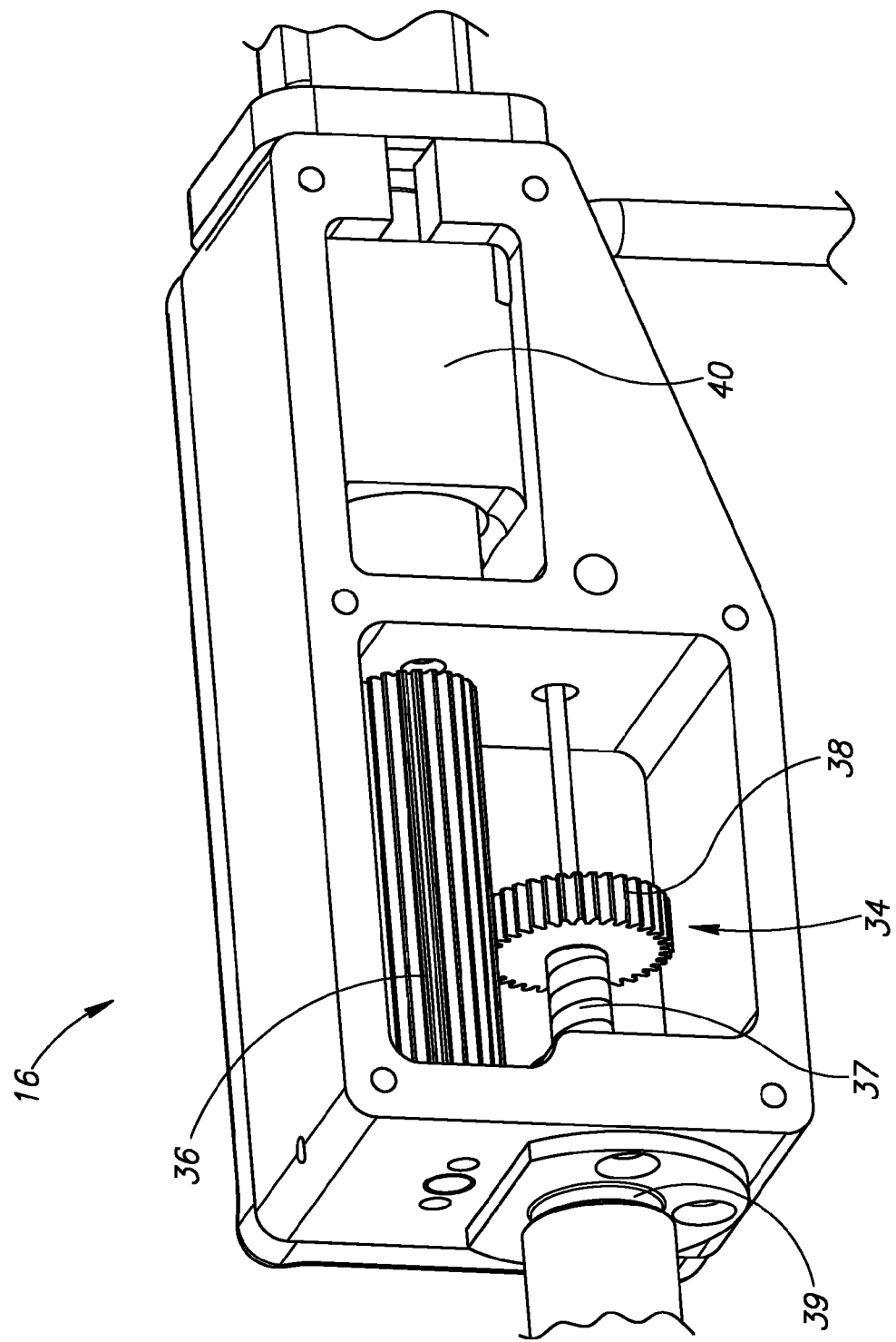
FIGS. 5A and 5B are perspective view illustrations of a middle portion of the device of FIG. 1, in accordance with embodiments of the present invention.
Figure 5B:
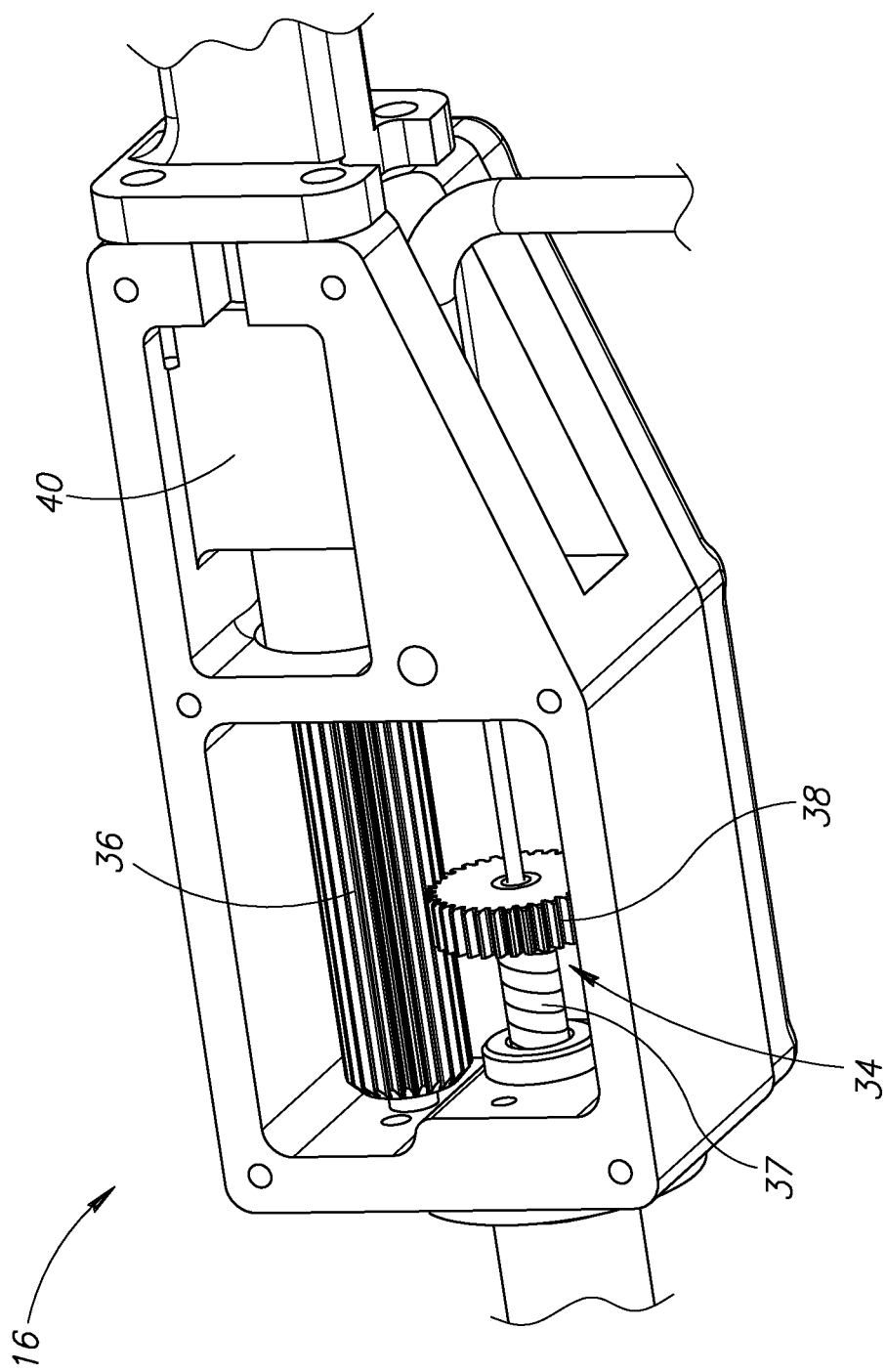

Reference is now made to FIGS. 5A and 5B, which are perspective views of middle portion 16 of device 10, in accordance with embodiments of the present invention. Side portions of housing 22 have been removed to reveal an inner mechanism of middle portion 16. Middle portion 16 includes a gear mechanism 34 having a pinion 36 and wheel 38 configuration. Further, wheel 38 is attached to a threaded bar 37. Threaded bar 37 is distal to wheel 38, and is positioned through a nut 39 which is attached to a distal portion of housing 22. Threaded bar 37 is at a proximal end of slicer 28. In one embodiment, threaded bar 37 is attached to a proximal end of slicer 28. In another embodiment, threaded bar 37 and slicer 28 comprise a unit, wherein threaded bar 37 comprises a proximal end of slicer 28. The disclosed configuration provides for translational motion at the same time and with the same mechanism as rotational motion. The speed of rotation and sizes of grooves on pinion 36 and wheel 38 determine a fixed relationship between the translational motion and rotational motion. In an alternative embodiment, a separate translational mechanism may be used, and translational and rotational movement may be separately controlled. It should be readily apparent that any other suitable gear mechanism may be used. In the embodiment shown herein, the gear mechanism is a combination rotational/translational mechanism, such that activation of gear mechanism 34 causes rotation and forward motion of slicer 28. Cryogenic needle 26 remains static while slicer 28 rotates and advances. In an embodiment wherein collection compartment 30 is sheath 31, sheath 31 remains static while slicer 28 rotates and advances, since sheath 31 is immovable with respect to middle portion 16. In an embodiment wherein collection compartment 30 is collection vial 33, collection vial 33 moves with slicer 28. A driving module 40 is housed in middle portion 16 and drives the pinion to generate the rotation and advancement of the slicer. Driving module 40 may be, for example, an electrical motor.

Reference is now made to FIG. 6, which is an expanded view of slicer 28 in accordance with one embodiment of the present invention, and a sample 32 resulting from a tissue portion sliced with slicer 28. In the embodiment shown in FIG. 6, slicer 28 has a helical flute configuration, similar to a rotating drill-bit. Slicer 28 includes cutting flutes 29 having particular dimensions so as to enable a thin sample to be obtained. In some embodiments, an outer diameter of slicer 28 may be in a range of 1-4 mm and more specifically may be approximately 3 mm, a diameter of cryogenic needle 26 may be in a range of 0.5-2 mm and more specifically may be approximately 1.5 mm, and the depth of flutes 29 may be in a range of 0.1-1 mm and more specifically may be approximately 0.5 mm. The invention is not limited to these ranges and smaller or larger dimensions may be advantageous in some circumstances. Sample 32 is a thin, spiral shaped sample. In some embodiments of the present invention, sample 32 has a thickness T of 50 micrometers or less, and more particularly a thickness T of approximately 10 micrometers so that it can be directly viewed under a microscope. In alternative embodiments, thicker slices can be sampled and then thin frozen sections may be cut in the pathology lab by using standard microtome apparatus.

Reference is now made to FIG. 7, which is a perspective illustration of slicer 28 in accordance with another embodiment of the present invention. Slicer 28 includes a cutting head 46. Cutting head 46 includes a body 48, one or multiple windows 50, and a blade 52 for each window 50. Collection compartment 30 in this embodiment is a collection vial 33 wherein slices obtained by cutting head 46 are collected in collection vial 33. Collection vial is positioned proximal to body 48 of cutting head 46 and may be attached thereto and is coaxial to cryogenic needle 26. Cutting head may be a rotating cutting head, and may include rotational and translational movement simultaneously, as described above with reference to FIG. 5. Alternatively, cutting head 46 may be configured to move translationally while blades 52 rotate. An example of a sample 32 which may be obtained by a rotating cutting head 46 is shown in FIG. 7.

Figure 8A:
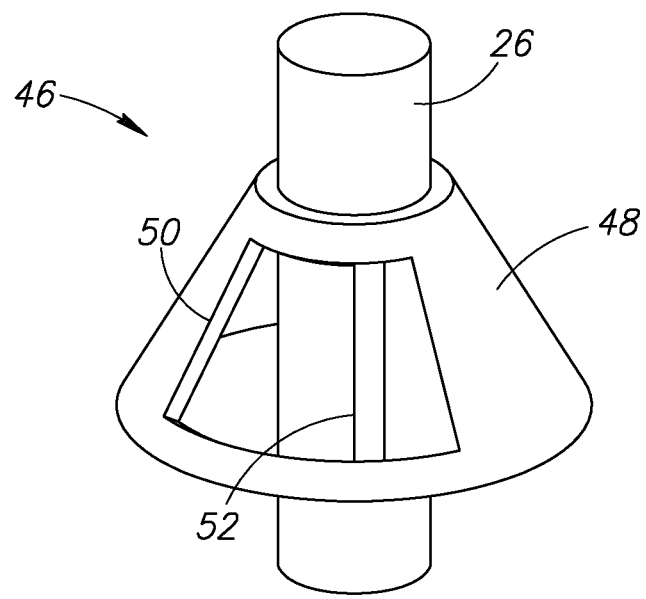
FIGS. 8A and 8B are enlarged views of the cutting head of FIG. 7, in accordance with embodiments of the present invention.
Figure 8B:
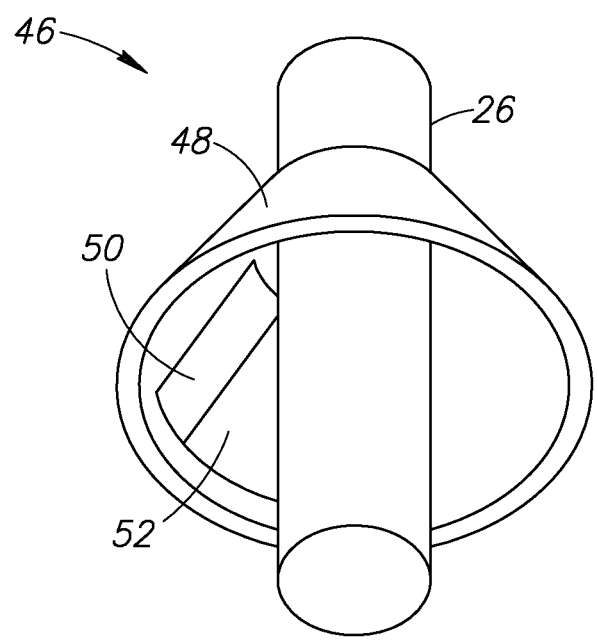

Reference is now made to FIGS. 8A and 8B, which are enlarged views of cutting head 46 in accordance with embodiments of the present invention. Cutting head 46 is positioned coaxial to cryogenic needle 26. In one embodiment, body 48 is configured to rotate about cryogenic needle 26. In another embodiment, blades 52 are configured to rotate through body 48 and cut the tissue through windows 50. Thus, either a continuous slab of sample 32 may be obtained, as shown in FIG. 7, or pieces or flakes of tissue may be obtained as sample 32 when the cutting is done through windows 50. In either case, sample 32 is thin enough to be viewed under a microscope, i.e. approximately 50 micrometers or less. Alternatively, thicker slices may be provided and later cut in the pathology lab.

Figure 9A:
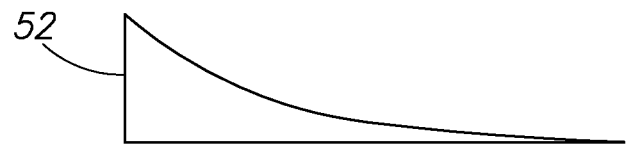
FIGS. 9A-9C are schematic illustrations of embodiments of a blade of the cutting head of FIGS. 8A and 8B, showing different configurations of the blade in accordance with embodiments of the present invention.
Figure 9B:
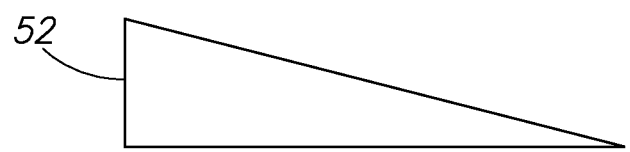
Figure 9C:
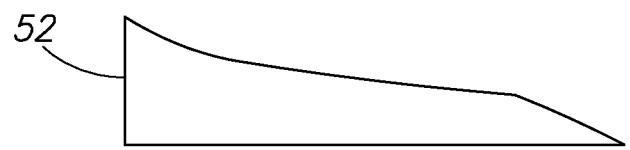

Reference is now made to FIGS. 9A-9C, which are schematic illustrations of embodiments of blade 52 having different shapes. For example, blade 52 may have a planar concave configuration, as in FIG. 9A. Alternatively, blade 52 may have a wedge configuration, as in FIG. 9B. In yet another embodiment, blade 52 may have a chisel shaped configuration as in FIG. 9C. In other embodiments, blade 52 may have other shapes and configurations, such that a thin sample having a thickness of 50 micrometers or less may be obtained. These shapes are similar to blades found in a microtome. The cutting mechanism is designed to enable frozen tissue to be cut around the cryogenic needle in a similar way that is currently used in the pathology lab to produce frozen sections with a microtome. By using a design similar to a microtome blade and adapting the design into a rotating cutting mechanism such as described herein, it is possible to obtain samples 32 comprised of tissue sections that have similar properties as achieved in frozen sections by a standard cryo-microtome apparatus. Since slicer 28 is positioned around cryogenic needle 26, the tissue to be sampled may remain in a frozen state during slicing. Slicer 28 may be designed so as to account for some sections of tissue being softer or less frozen than others. For example, a torque sensor may be positioned on slicer 28, wherein the torque sensor can sense the torque applied by motor 40 on slicer 28 during slicing. As the torque changes in accordance with properties of the tissue, the rotation and/or forward advance speed can be adjusted accordingly—either manually or via an automated feedback loop with a processor.

Slicer 28 may be configured to cut a thin layer of deep-frozen tissue in a way similar to the cutting of solid materials (metals, plastic) by a drill milling machine or by a microtome. Rotation speed of slicer 28, as well as advancement speed of forward motion of slicer 28 and design of blade 52 or cutting grooves 29 all help to determine the section thickness. The resulting tissue sample is a continuous, thin slab of tissue that may remain intact or brake into small flakes that are then pushed into collection compartment 30.

In some embodiments, device 10 may be comprised of a flexible material, thereby providing a flexible cryogenic biopsy device for use through an endoscope, for example. Cryogenic needle 26 may be flexible as well.

Figure 10:
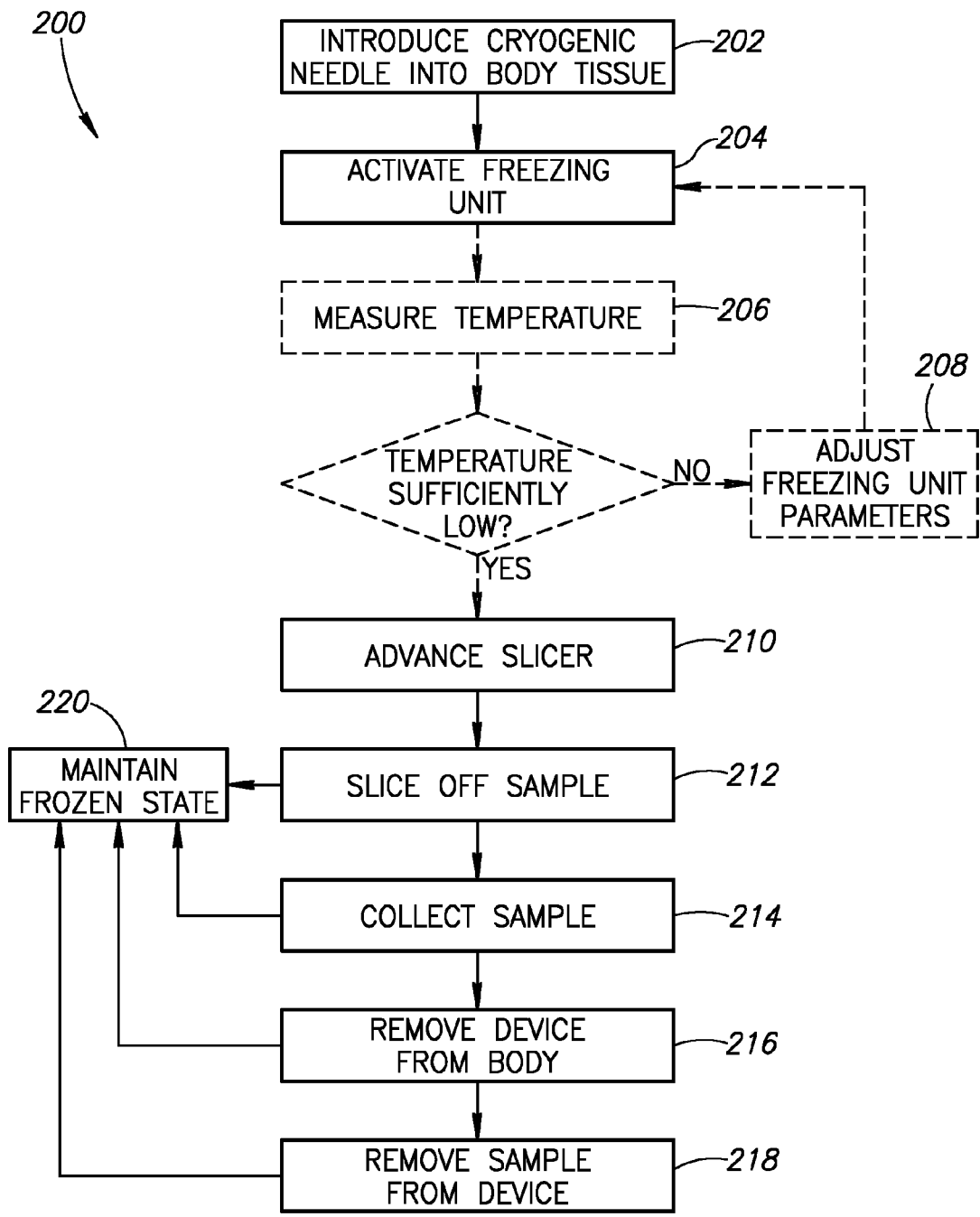
FIG. 10 is a flow-chart illustration showing the steps of a method of obtaining a biopsy sample, in accordance with embodiments of the present invention.

Reference is now made to FIG. 10, which is a flow-chart illustration showing the steps of a method 200 of obtaining a biopsy sample, in accordance with embodiments of the present invention. In a biopsy procedure using device 10, cryogenic needle 26 is introduced (step 202) into the body tissue by pushing device 10 into the body as in known biopsy procedures. Freezing unit 100 is activated (step 204). In some embodiments, sensor 110 measures (step 206) a temperature at needle tip 60. If the temperature is not low enough, freezing unit parameters are adjusted (step 208) in some embodiments using processor 104. A range of suitable temperatures may be −10 to −50 degrees Celsius, and in some embodiments approximately −30 degrees Celsius. With device 10 in place, slicer 28 is advanced (step 210) over cryogenic needle 26 into the tissue. Advancement may be done manually or via a motorized mechanism. In some embodiments, slicer 28 is rotatably advanced into the tissue. In other embodiments, slicer is advanced translationally and blades 52 are rotated, either by rotating cutting head 46 or by rotating blades 52 themselves. A sample 32 of tissue is sliced off (step 212) by the rotating motion. Collecting compartment 30 then collects (step 214) sample 32. In one embodiment, collecting is done by retracting slicer 28 so that it moves proximally into sheath 31, thereby enclosing the sliced tissue therein. In another embodiment, collecting is done by advancing device distally, thereby pushing sample 32 into collection vial 33. The entire device 10 with sample 32 therein is then removed (step 216) from the body, and the sample is removed (step 218) from inside collection compartment 30.

A particular feature of the present invention is that samples 32 obtained via device 10 may be directly viewed under a microscope and screened for further biomarker testing, thus increasing sensitivity of the biomarker analysis.

In order to obtain samples which are suitable for immediate viewing, samples 32 in one embodiment have a thickness of 50 micrometers or less. In some embodiments, samples 32 have a thickness of 10 micrometers or less. In yet another embodiment, samples 32 have a thickness of more than 50 micrometers, and are sliced before viewing with a microscope. Moreover, samples 32 must be maintained (step 220) in a frozen state throughout the method, including during collecting, removal from the device, viewing, and analyzing. When the biopsy procedure is completed, and device 10 is extracted from the body, samples 32 may remain in a deep-frozen state by continued operation of the cryogenic system. Once out of the body, samples 32 may be stored in a container and placed in a frozen environment. In one embodiment, the container is collection vial 33, which is released from device 10, capped, and inserted into a liquid nitrogen container, for example. Samples 32 may remain frozen during viewing by using a microscope with a cryo-chamber.

A potential difficulty is adhesion of the tissue slabs or flakes into a "conglomerate" of tissue sections. Although the tissue samples may remain non-sticky as long as they are kept in a deep frozen state, if this problem arises, a solution would be to use a micro strip dispenser to collect the continuous slab of tissue that is cut by slicer 28. A similar approach on a larger scale is used in ultramicrotomes for better handling of extremely thin sections prepared for transmission electron microscopy. This approach can also facilitate the processing of the tissue samples in the pathology laboratory and to enable automatic processing of the biopsy samples in the long run.

Figure 11:
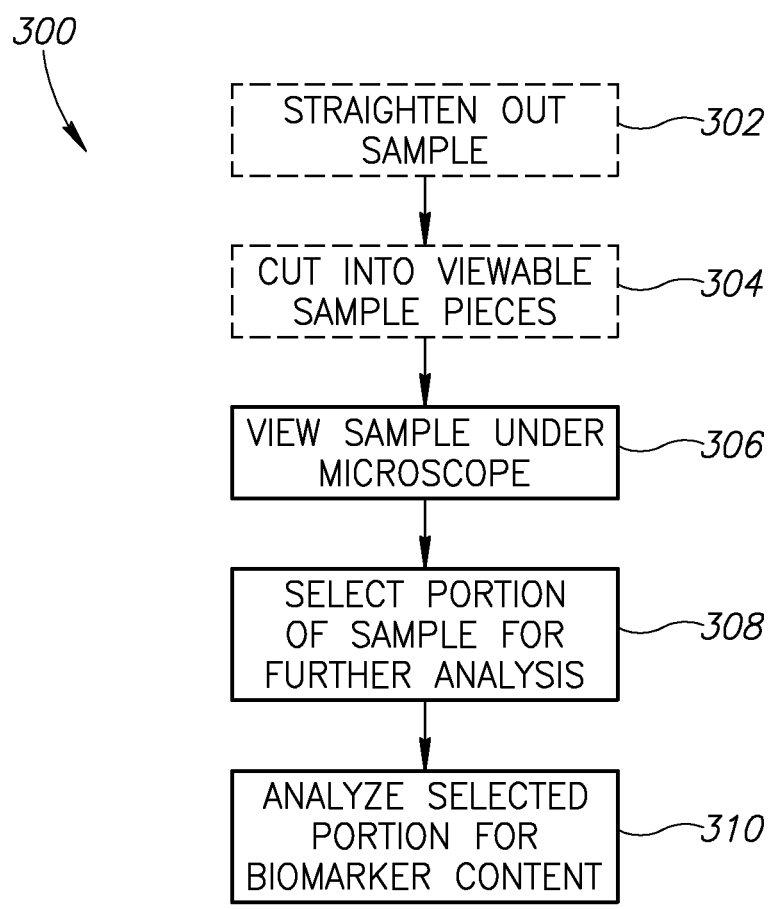
FIG. 11 is a flow-chart illustration of steps of a method of analyzing a sample obtained from the device of FIG. 1, in accordance with embodiments of the present invention.
Figure 12:
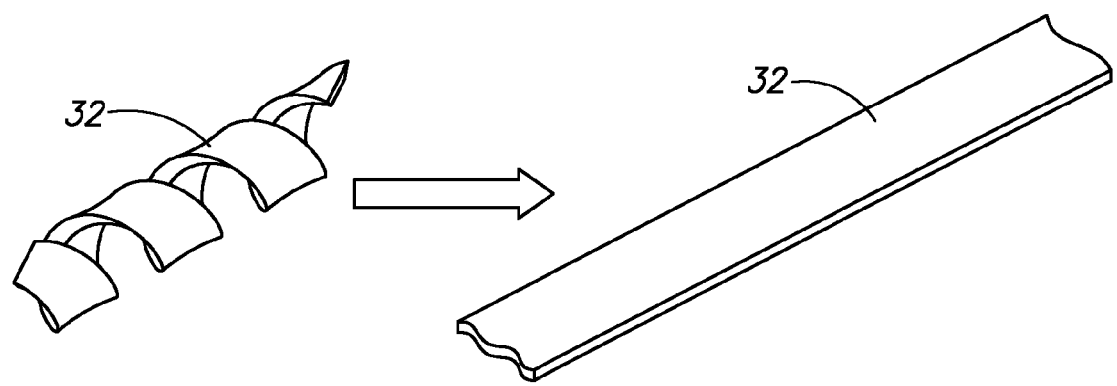
FIG. 12 is an illustration of a curled or helical shaped sample being straightened out in accordance with one of the steps of the method of FIG. 11.
Figure 13:
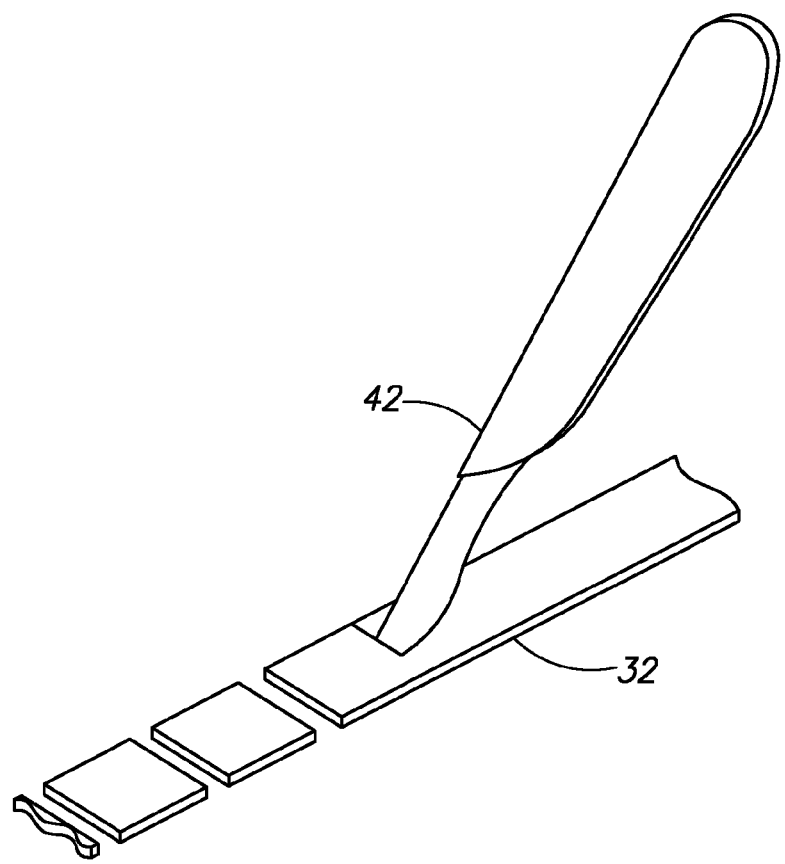
FIG. 13 is an illustration of the sample of FIG. 12 being cut into viewable sample pieces.
Figure 14:
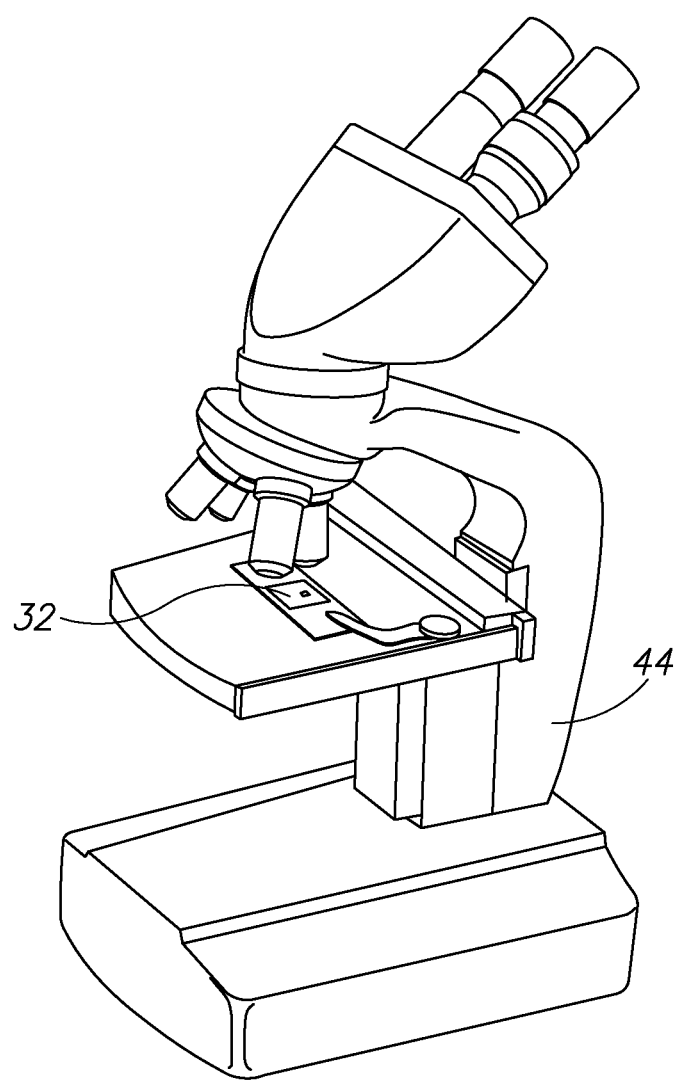
FIG. 14 is an illustration of the viewable samples of FIG. 13 being viewed under a microscope.

Reference is now made to FIG. 11, which is a flow-chart illustration of steps of a method 300 of analyzing a sample 32 obtained from device 10, together with FIGS. 12, 13 and 14, which are schematic illustrations showing some of the steps of method 300, in accordance with embodiments of the present invention. In one embodiment, sample 32 is a continuous slab of tissue, that can be cut into viewable pieces. In some instances, sample 32 may initially be in a curled or helical configuration as shown in FIGS. 6 and 7 as a result of the helical flute configuration of slicer 28, or the cutting head 46 and shape of blade 52. As shown in FIG. 12, a curled or helical or any other shape of sample 32 may be straightened out (step 302), and then cut (step 304) into viewable sample pieces using a knife 42 or any other cutting means, as shown in FIG. 13. The viewable samples may then be viewed (step 306) under a microscope 44, as shown in FIG. 14. Alternatively, the samples may be viewed in a continuous slab and during or after viewing cut into pieces. In another embodiment, sample 32 is broken into small flakes during collection. In this case, sample 32 may be viewed under a microscope without further straightening or cutting.

Returning to FIG. 11, next, a portion of the frozen sample is selected (step 308) for further analysis. This can either be done by a user viewing the samples under the microscope and manually selecting each sample, or by an automated system which is configured to select samples based on viewing content. Selection is done based on the content (i.e. an amount of pathological tissue versus an amount of healthy tissue). The selection allows for more homogenous tissue samples to be analyzed, without the "noise" of healthy tissue. To date, methods for tissue analysis following biopsy have been limited to either microscopy or biomarker analysis. The present invention provides both methods for a single biopsy procedure. Moreover, current methods for biomarker analysis do not provide selection of samples based on histology since generally when biomarker analysis is done, histological analysis of the same specimens is not done. An advantage of having both methods of analysis for one procedure is that more accurate results for biomarker analysis may be obtained via histologic-based selection. Thus, sensitivity is enhanced by providing more homogenous tissue samples.

The selected portion is then analyzed (step 310) for biomarker content to determine the pathological parameters of the sample. In some embodiments, the selected sample portion is processed into tissue homogenate and then analyzed for biomarker content. In other embodiments, the selected sample portion is analyzed for biomarker content from intact tissue samples.

In some embodiments, cryogenic needle 26 can be used for biopsy as described above, and then afterwards used for cryoablation. Thus, for example, in one embodiment, after cutting a tissue sample using slicer 28, slicer 28 can be retracted, and cryogenic needle can be advanced into the tissue to perform cryoablation.

Standard biopsy procedures provide tissue samples that retain tissue histology and thus enable the analysis of tissue and cellular morphology and evaluation of biomarkers by histology based methods like IHC, FISH. In standard biopsy procedures, the evaluation of the content of biomarkers in the tissue does not involve preservation of tissue histology and is based on tissue homogenate methodologies. The cryogenic biopsy device of the present invention harvests tissue samples in a way that enables standard tissue histology analysis, histology-based biomarker analysis, and homogenate-based biomarker analysis. It is a particular feature of the present invention that the tissue harvesting is conducted after the tissue to be sampled is deep frozen, thus maintaining the bio-molecular profile of the intact tissue.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall within the true spirit of the present invention.

What is claimed is:

1. A biological tissue acquisition, preservation, and biomarker analysis system, the system comprising:
   a freezing unit;
   a cryogenic biopsy device in communication with said freezing unit, said cryogenic biopsy device comprising:
      a cryogenic needle having a needle tip configured to penetrate a tissue to be sampled and configured to freeze the tissue by said freezing unit prior to removal of the tissue;
      a slicer positioned coaxial to said cryogenic needle, said slicer configured to slice a sample of the frozen tissue to a thickness which is sufficiently thin such that the frozen sliced sample of tissue is suitable for microscopy analysis, while continuously maintaining a frozen state of the frozen tissue; and
      a collection and preservation compartment for collecting the sliced samples of tissue, said collection and preservation compartment configured to continuously maintain a frozen state of the sliced samples after the frozen tissue is removed from the cryogenic needle, wherein the maintained frozen state is at a temperature which is suitable for biomarker analysis;
   a device for histological analysis of the frozen sliced samples; and
   a biomarker analysis mechanism for analysis of preselected frozen samples having a relatively high amount of pathological tissue as determined by the histological analysis.

2. The biological tissue acquisition, preservation, and biomarker analysis system of claim 1, wherein said freezing unit comprises a freezing substance compartment and a processor.

3. The biological tissue acquisition, preservation, and biomarker analysis system of claim 2, further comprising a sensor positioned on said cryogenic needle, wherein said sensor is in electronic communication with said processor and configured to provide feedback to said processor, and wherein said processor is configured to regulate a freezing temperature based on said feedback.

4. The biological tissue acquisition, preservation, and biomarker analysis system of claim 1, wherein said slicer has a cutting head and blades.

5. The biological tissue acquisition, preservation, and biomarker analysis system of claim 1, wherein said slicer is configured to provide frozen tissue samples having a thickness of 50 micrometers or less.

6. The biological tissue acquisition, preservation, and biomarker analysis system of claim 1, wherein said slicer is configured to provide frozen tissue samples having a thickness of 10 micrometers or less.

7. The biological tissue acquisition, preservation, and biomarker analysis system of claim 1, further comprising an automated selector for selecting samples for biomarker analysis based on histological analysis of said frozen samples.

8. The biological tissue acquisition, preservation, and biomarker analysis system of claim 1, wherein said freezing unit is configured to freeze a tissue sample at a temperature of approximately −30 degrees Celsius.

9. The biological tissue acquisition, preservation, and biomarker analysis system of claim 1, wherein said device for histological analysis is a microscope.

10. The system of claim 1, wherein the freezing unit is an external unit and is configured to provide a freezing substance to the cryogenic biopsy device in an amount such that the sampled tissue remains frozen from a time of sampling until after removal of the sample from the cryogenic biopsy device.

11. A biological tissue acquisition, preservation, and biomarker analysis system, the system comprising:
   a freezing unit, wherein the freezing unit is an external unit and is configured to provide a freezing substance to the cryogenic biopsy device in an amount such that the sampled tissue remains frozen from a time of sampling until after removal of the sample from the cryogenic biopsy device;
   a cryogenic biopsy device in communication with said freezing unit, said cryogenic biopsy device comprising:
      a cryogenic needle having a needle tip configured to penetrate a tissue to be sampled and configured to freeze the tissue by said freezing unit prior to removal of the tissue;
      a slicer positioned coaxial to said cryogenic needle, said slicer configured to slice a sample of the frozen tissue while continuously maintaining a frozen state of the frozen tissue; and
      a collection and preservation compartment for collecting the sliced samples of tissue, said collection and preservation compartment configured to continuously maintain a frozen state of the sliced samples after the frozen tissue is removed from the cryogenic needle, wherein the maintained frozen state is at a temperature which is suitable for biomarker analysis;

a device for histological analysis of the frozen sliced samples; and a biomarker analysis mechanism for analysis of pre-selected frozen samples having a relatively high amount of pathological tissue as determined by the histological analysis.

12. The biological tissue acquisition, preservation, and biomarker analysis system of claim 11, wherein said freezing unit comprises a freezing substance compartment and a processor.

13. The biological tissue acquisition, preservation, and biomarker analysis system of claim 11, further comprising a sensor positioned on said cryogenic needle, wherein said sensor is in electronic communication with said processor and configured to provide feedback to said processor, and wherein said processor is configured to regulate a freezing temperature based on said feedback.

14. The biological tissue acquisition, preservation, and biomarker analysis system of claim 11, wherein said slicer has a cutting head and blades.

15. The biological tissue acquisition, preservation, and biomarker analysis system of claim 11, wherein said slicer is configured to slice a sample of the frozen tissue to a thickness which is sufficiently thin such that the frozen sliced sample of tissue is suitable for microscopy analysis, while continuously maintaining a frozen state of the frozen tissue.

16. The biological tissue acquisition, preservation, and biomarker analysis system of claim 11, wherein said slicer is configured to provide frozen tissue samples having a thickness of 50 micrometers or less.

17. The biological tissue acquisition, preservation, and biomarker analysis system of claim 11, wherein said slicer is configured to provide frozen tissue samples having a thickness of 10 micrometers or less.

18. The biological tissue acquisition, preservation, and biomarker analysis system of claim 11, further comprising an automated selector for selecting samples for biomarker analysis based on histological analysis of said frozen samples.

19. The biological tissue acquisition, preservation, and biomarker analysis system of claim 11, wherein said freezing unit is configured to freeze a tissue sample at a temperature of approximately −30 degrees Celsius.

20. The biological tissue acquisition, preservation, and biomarker analysis system of claim 11, wherein said device for histological analysis is a microscope.

* * * * *